(12) United States Patent
Glezer et al.

(10) Patent No.: US 11,242,570 B2
(45) Date of Patent: Feb. 8, 2022

(54) CO-BINDER ASSISTED ASSAY METHODS

(71) Applicant: Meso Scale Technologies, LLC., Rockville, MD (US)

(72) Inventors: Eli N. Glezer, Del Mar, CA (US); George Sigal, Rockville, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 0 days.

(21) Appl. No.: 15/696,953

(22) Filed: Sep. 6, 2017

(65) Prior Publication Data

US 2017/0362668 A1    Dec. 21, 2017

Related U.S. Application Data

(62) Division of application No. 14/357,653, filed as application No. PCT/US2012/064263 on Nov. 9, 2012, now Pat. No. 9,777,338.

(60) Provisional application No. 61/558,537, filed on Nov. 11, 2011.

(51) Int. Cl.
| | |
|---|---|
| *C12Q 1/70* | (2006.01) |
| *C12Q 1/6813* | (2018.01) |
| *G01N 33/542* | (2006.01) |
| *G01N 33/543* | (2006.01) |
| *C12Q 1/6834* | (2018.01) |

(52) U.S. Cl.
CPC ............. *C12Q 1/70* (2013.01); *C12Q 1/6813* (2013.01); *C12Q 1/6834* (2013.01); *G01N 33/542* (2013.01); *G01N 33/54333* (2013.01)

(58) Field of Classification Search
CPC combination set(s) only.
See application file for complete search history.

(56) References Cited

U.S. PATENT DOCUMENTS

| | | |
|---|---|---|
| 5,093,268 A | 3/1992 | Leventis et al. |
| 5,147,806 A | 9/1992 | Kamin et al. |
| 5,200,314 A | 4/1993 | Urdea |
| 5,238,808 A | 8/1993 | Bard et al. |
| 5,240,863 A | 8/1993 | Shibue et al. |
| 5,308,754 A | 5/1994 | Kankare et al. |
| 5,324,457 A | 6/1994 | Zhang et al. |
| 5,589,136 A | 12/1996 | Northrup et al. |
| 5,591,581 A | 1/1997 | Massey et al. |
| 5,597,910 A | 1/1997 | Gudibande et al. |
| 5,641,623 A | 6/1997 | Martin |
| 5,643,713 A | 7/1997 | Liang et al. |
| 5,679,519 A | 10/1997 | Oprandy |

(Continued)

FOREIGN PATENT DOCUMENTS

| | | |
|---|---|---|
| JP | 2006-511807 A | 4/2006 |
| JP | 2007-525661 A | 9/2007 |

(Continued)

OTHER PUBLICATIONS

Weibrecht et al. Expert Rev. Proteomics 2010 vol. 7, p. 401-409 (Year: 2010).*

(Continued)

*Primary Examiner* — Changhwa J Cheu
(74) *Attorney, Agent, or Firm* — Scully, Scott, Murphy & Presser, P.C.

(57) ABSTRACT

The present invention is directed to methods for reducing cross-reactivity between species employed in multiplexed immunoassays.

34 Claims, 2 Drawing Sheets

(56) References Cited

U.S. PATENT DOCUMENTS

| | | | |
|---|---|---|---|
| 5,705,402 | A | 1/1998 | Leland et al. |
| 5,731,147 | A | 3/1998 | Bard et al. |
| 5,776,672 | A | 7/1998 | Hashimoto et al. |
| 5,786,141 | A | 7/1998 | Bard et al. |
| 5,846,485 | A | 12/1998 | Leland et al. |
| 5,866,434 | A | 2/1999 | Massey et al. |
| 6,066,448 | A | 5/2000 | Wohlstadter et al. |
| 6,136,268 | A | 10/2000 | Ala-Kleme et al. |
| 6,207,369 | B1 | 3/2001 | Wohlstadter et al. |
| 6,214,552 | B1 | 4/2001 | Heroux et al. |
| 6,673,533 | B1 | 1/2004 | Wohlstadter et al. |
| 6,709,815 | B1 | 3/2004 | Dong et al. |
| 6,939,720 | B2 | 9/2005 | Chandler et al. |
| 7,932,060 | B2 * | 4/2011 | Nadeau ............... C12Q 1/6851 435/6.1 |
| 2004/0121382 | A1 | 6/2004 | Liu et al. |
| 2004/0142323 | A1 | 7/2004 | Boyde |
| 2004/0209261 | A1 | 10/2004 | Keys et al. |
| 2004/0248103 | A1 | 12/2004 | Feaver et al. |
| 2005/0003432 | A1 | 1/2005 | Hall et al. |
| 2009/0176318 | A1 | 7/2009 | Kolpashchikov |
| 2010/0261292 | A1 | 10/2010 | Glezer et al. |
| 2013/0059741 | A1 | 3/2013 | Weiner |
| 2014/0315189 | A1 | 10/2014 | Glezer et al. |

FOREIGN PATENT DOCUMENTS

| | | |
|---|---|---|
| WO | 97/36931 A1 | 10/1997 |
| WO | 98/12539 A1 | 3/1998 |
| WO | 98/57154 A1 | 12/1998 |
| WO | 99/14599 A1 | 3/1999 |
| WO | 99/32662 A1 | 7/1999 |
| WO | 99/58962 A1 | 11/1999 |
| WO | 99/63347 A2 | 12/1999 |
| WO | 00/03233 A1 | 1/2000 |
| WO | 2004/061131 A1 | 7/2004 |
| WO | 2005/059509 A2 | 6/2005 |
| WO | 2009/067009 A1 | 5/2009 |
| WO | 2010/059820 A1 | 5/2010 |
| WO | 2011/047087 A2 | 4/2011 |

OTHER PUBLICATIONS

Chan (Immunoassay A Practical Guide 1987, chapter 1, total 7 pages). (Year: 1987).*

Darmanis S. et al., "ProteinSeq: High-Performance Proteomic Analyses by Proximity Ligation and Next Generation Sequencing", Plos One 6(9):e25583 (Sep. 29, 2011).

Fredriksson S. et al., "Protein Detection Using Proximity-Dependent DNA Ligation Assays", Nature Biotechnology 20:473-477 (May 1, 2002).

Heyduk E. et al., "Molecular Pincers: Antibody-Based Homogeneous Protein Sensors", Analytical Chemistry 80(13):5152-5159 (Jul. 1, 2008).

Hochman J. et al., "An Active Antibody Fragment (Fv) Composed of the Variable Portions of Heavy and Light Chains", Biochemistry 12(6):1130-1135 (1973).

Hu J. et al., "Quantitation of Femtomolar Protein Levels Via Direct Readout With the Electrochemical Proximity Assay", Journal of the American Chemical Society 134(16):7066-7072 (Mar. 27, 2012).

Porter R.R. et al., "Subunits of Immunoglobulins and Their Relationship to Antibody Specificity", J. Cell Physiol. 67: Sup. 1:51-64 (1966).

Söderberg O. et al., "Characterizing Proteins and Their Interactions in Cells and Tissues Using the In Situ Proximity Ligation Assay", Methods 45(3):227-232 (Jul. 1, 2008).

Tavoosidana G. et al., "Multiple Recognition Assay Reveals Prostasomes as Promising Plasma Biomarkers for Prostate Cancer", PNAS 108(21):8809-8814 (May 24, 2011).

Extended Supplementary Partial European Search Report dated Nov. 3, 2015 received from European Application No. 12 84 8432.6.

International Search Report dated Mar. 15, 2013 received in PCT/US2012/064263.

Japanese Notice of Reasons for Rejection dated Aug. 16, 2016 received in Japanese Application No. 2014-541281, together with an English-language translation.

U.S. Non-Final Office Action dated Jan. 31, 2017 received in U.S. Appl. No. 14/357,653.

U.S. Final Office Action dated Jun. 22, 2016 received in U.S. Appl. No. 14/357,653.

U.S. Non-Final Office Action dated Oct. 26, 2015 received in U.S. Appl. No. 14/357,653.

Extended European Search Report dated Jan. 7, 2019 received in European Patent Application No. 18 19 2525.6.

European Office Action dated Jan. 27, 2020 received in European Application No. 18 192 525.6.

Japanese Decision of Rejection dated Jan. 7, 2020 received in Japanese Patent Application No. 2017-231321, together with an English-language translation.

Japanese Office Action dated Mar. 16, 2021 received in Japanese Application No. 2020-079957, together with an English-language translation.

* cited by examiner

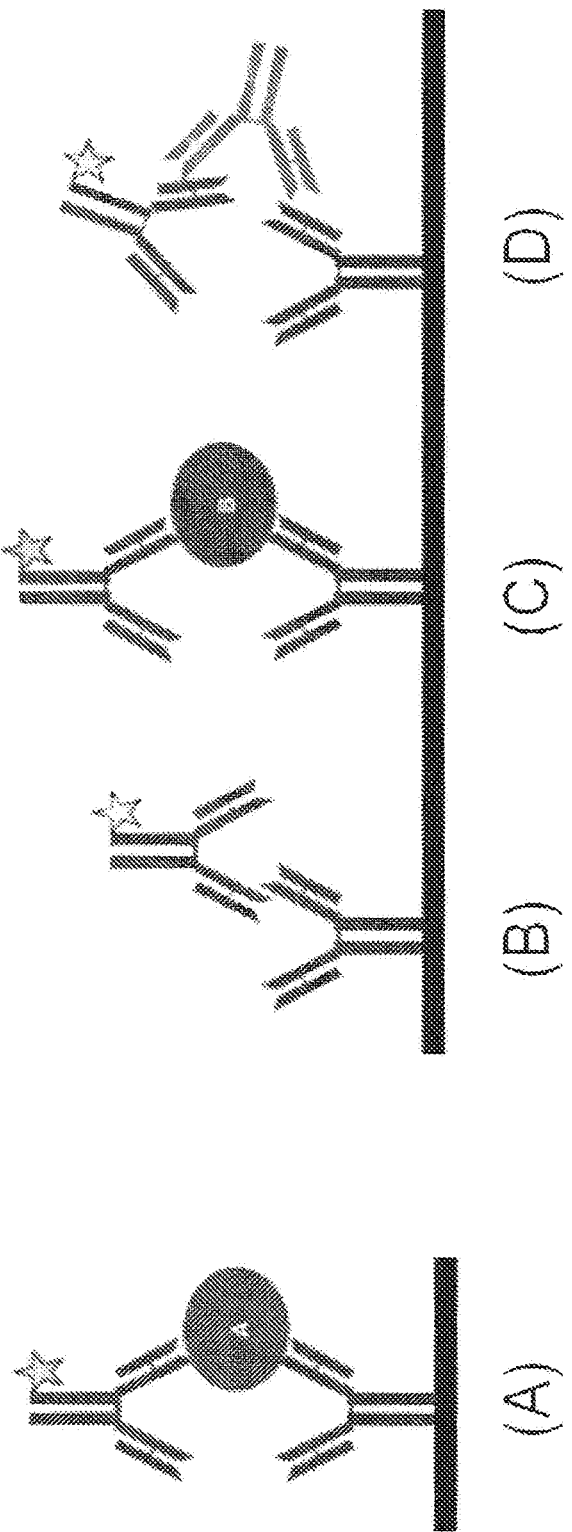
FIGS. 1A-D

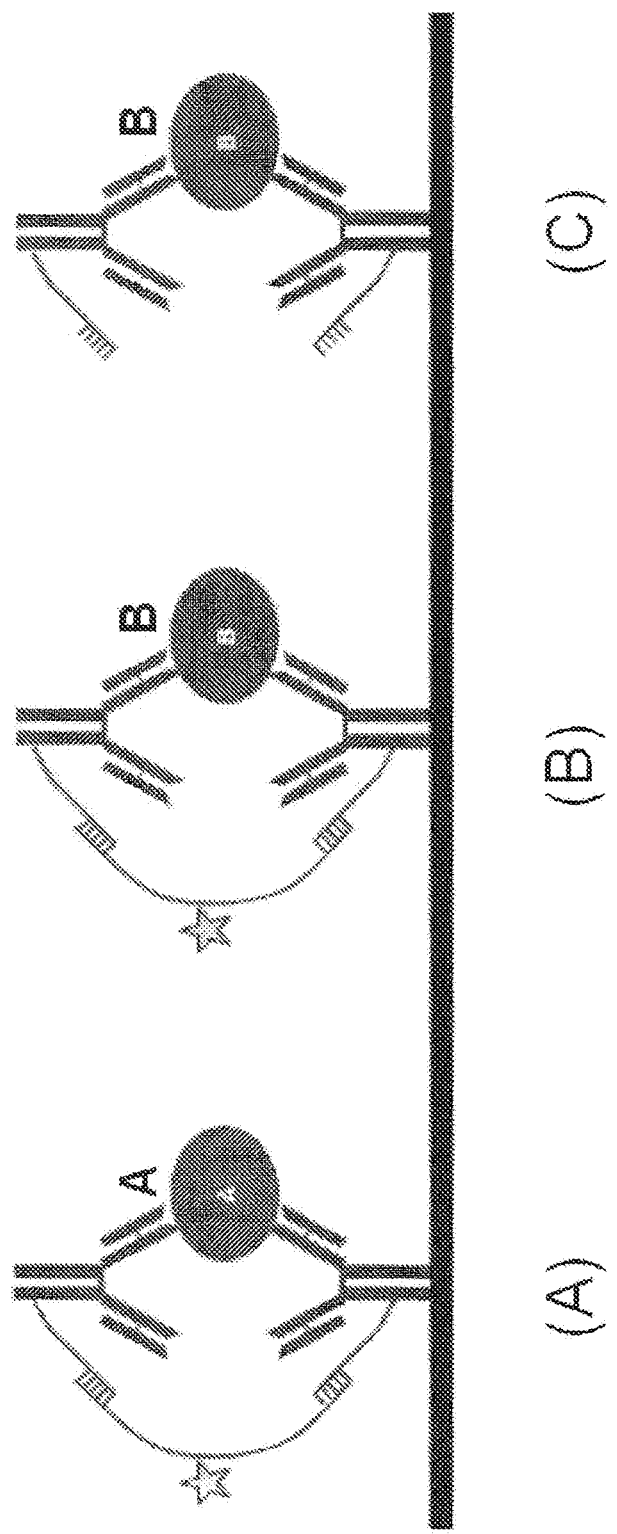
FIGS. 2A-C

CO-BINDER ASSISTED ASSAY METHODS

CROSS REFERENCE TO RELATED APPLICATIONS

The present application is a divisional of copending U.S. patent application Ser. No. 14/357,653, filed May 12, 2014, which is a 371 of International application having Serial No. PCT/US2012/064263, filed Nov. 9, 2012, which claims the benefit of U.S. Provisional Application No. 61/558,537, filed Nov. 11, 2011, the entire contents of which are incorporated herein by reference.

FIELD OF THE INVENTION

The present invention is directed to methods for conducting immunoassays. The methods are particularly well suited for reducing cross-reactivity between species employed in immunoassays, e.g., antibodies and antigens.

BACKGROUND OF THE INVENTION

A substantial body of literature has been developed concerning techniques that employ binding reactions, e.g., antigen-antibody reactions, nucleic acid hybridization and receptor-ligand reactions, for the sensitive measurement of analytes of interest in samples. The high degree of specificity in many biochemical binding systems has led to many assay methods and systems of value in a variety of markets including basic research, human and veterinary diagnostics, environmental monitoring and industrial testing. The presence of an analyte of interest may be measured by directly measuring the participation of the analyte in a binding reaction. In some approaches, this participation may be indicated through the measurement of an observable label attached to one or more of the binding materials.

One of the challenges with immunoassay measurements is the potential for cross-reactivity among antibodies and analytes. Cross-reactivity can lead to higher backgrounds, reduced sensitivity, and influence the detection of one analyte in a plurality. In a multiplexed immunoassay with N capture antibodies and N detection antibodies, there are N×N potential antibody interactions (including non-specific binding interactions). Therefore, in a 25-plex assay, there are 625 possible interactions. While antibodies are typically highly specific for a particular analyte, undesired interactions are common and have to be screened out when formulating a multiplexed assay panel. Finding antibodies that work well in a multiplexed format becomes increasingly challenging as the degree of multiplexing is increased.

In a multiplexed sandwich immunoassay format, the analyte specificity is provided by the capture antibody. As shown in FIG. 1(a), if the capture antibody (bound to a surface) and labeled detection antibody each bind to analyte A, A is detected in the assay. However, as shown in FIGS. 1 (b)-(d), undesired interactions between capture and detection antibodies (1(b)), capture antibody and analyte B (1(c)), or capture and detection antibodies and an additional antibody present in the sample (1(d)) can result. If a capture antibody cross-reacts with another species in the sample, e.g., as shown in FIG. 1(b)-(d), the resulting signal can be misinterpreted as the presence of the target analyte, yielding a false positive result.

In addition, complex matrices, such as human serum/plasma and cell lysates, may contain molecules or molecular complexes that will crosslink capture antibodies to detection antibodies. This is particularly problematic as the effect is unpredictable (unlike direct antibody-antibody cross reactivity), and it can lead to falsely elevated measurements of a particular analyte. One example of a class of matrix-mediated cross-reactivity is human anti-mouse antibodies (knows as a HAMA effect), or other human anti-animal antibodies. When anti-mouse antibodies are present in human serum, they can bind to mouse-derived antibodies that are typically used in immunoassays, and potentially form a bridge between capture and detection antibodies, falsely mimicking the presence of an analyte. While this problem is relevant in single analyte immunoassays, it is exacerbated by a factor of N2 in multiplexed immunoassays where N detection antibodies can be bridged to N capture antibodies.

SUMMARY OF THE INVENTION

Accordingly, the present invention provides a method of conducting a binding assay comprising: (a) contacting a sample comprising an analyte of interest with (i) a solid surface including a first binding reagent immobilized thereto comprising a first binding region that binds to said analyte of interest, wherein said first binding reagent is linked to a first linking agent comprising a first oligonucleotide sequence and (ii) a second binding reagent comprising a second binding region that binds to said analyte of interest, wherein said second binding reagent is linked to a second linking agent comprising a second oligonucleotide sequence, wherein said second oligonucleotide sequence comprises a sequence complementary to at least a portion of said first oligonucleotide sequence; wherein said contacting step is conducted under conditions wherein said first and second binding regions bind to said analyte and said first oligonucleotide sequence hybridizes to said second oligonucleotide sequence; and (b) measuring the amount of said analyte bound to said solid support.

In an alternative embodiment, the invention contemplates a method of conducting a binding assay comprising: (a) contacting a sample comprising an analyte of interest with a solid surface including a first binding reagent immobilized thereto comprising a first binding region that binds to said analyte of interest, wherein said first binding reagent is linked to a first linking agent comprising a first oligonucleotide sequence; (b) contacting the mixture formed in step (a) with a second binding reagent comprising a second binding region that binds to said analyte of interest, wherein said second binding reagent is linked to a second linking agent comprising a second oligonucleotide sequence, wherein said second oligonucleotide sequence comprises a sequence complementary to at least a portion of said first oligonucleotide sequence; wherein said contacting step (b) is conducted under conditions wherein said first and second binding regions bind to said analyte and said first oligonucleotide sequence hybridizes to said second oligonucleotide sequence; and (b) measuring the amount of said analyte bound to said solid support.

In one embodiment, the invention includes a method of conducting a binding assay comprising: (a) contacting a sample comprising an analyte of interest with (i) a solid surface including a first binding reagent immobilized thereto comprising a first binding region that binds to said analyte of interest, wherein said first binding reagent is linked to a first linking agent comprising a first oligonucleotide sequence; (ii) a second binding reagent comprising a second binding region that binds to said analyte of interest, wherein said second binding reagent is linked to a second linking agent comprising a second oligonucleotide sequence, and (iii) a bridging oligonucleotide sequence comprising a sequence complementary to at least a portion of said first oligonucleotide sequence and said second oligonucleotide sequence; wherein said contacting step is conducted under conditions wherein said first and second binding regions bind to said analyte and said bridging oligonucleotide sequence hybridizes to said first oligonucleotide sequence and said second oligonucleotide sequence; and (b) measuring the amount of said analyte bound to said solid support.

Still further, the invention includes a method of conducting a binding assay comprising: (a) contacting a sample comprising an analyte of interest with (i) a solid surface including a first binding reagent immobilized thereto comprising a first binding region that binds to said analyte of interest, wherein said first binding reagent is linked to a first linking agent comprising a first oligonucleotide sequence; and (ii) a second binding reagent comprising a second binding region that binds to said analyte of interest, wherein said second binding reagent is linked to a second linking agent comprising a second oligonucleotide sequence, wherein said contacting step (a) is conducted under conditions wherein said first and second binding regions bind to said analyte; (b) contacting the mixture formed in step (b) with a bridging oligonucleotide sequence comprising a sequence complementary to at least a portion of said first oligonucleotide sequence and said second oligonucleotide sequence; wherein said contacting step (c) is conducted under conditions wherein said bridging oligonucleotide sequence hybridizes to said first oligonucleotide sequence and said second oligonucleotide sequence; and (d) measuring the amount of said analyte bound to said solid support.

Moreover, the invention provides a method of conducting a binding assay comprising: (a) contacting a sample comprising an analyte of interest with (i) a solid surface including a first binding reagent immobilized thereto comprising a first binding region that binds to said analyte of interest, wherein said first binding reagent is linked to a first linking agent comprising a first oligonucleotide sequence, wherein said contacting step (a) is conducted under conditions wherein said first binding region that binds to said analyte; (b) contacting the mixture formed in step (a) with a second binding reagent comprising a second binding region that binds to said analyte of interest, wherein said second binding reagent is linked to a second linking agent comprising a second oligonucleotide sequence, wherein said contacting step (b) is conducted under conditions wherein said second binding region that binds to said analyte; (c) contacting the mixture formed in step (b) with a bridging oligonucleotide sequence comprising a sequence complementary to at least a portion of said first oligonucleotide sequence and said second oligonucleotide sequence; wherein said contacting step (c) is conducted under conditions wherein said bridging oligonucleotide sequence hybridizes to said first oligonucleotide sequence and said second oligonucleotide sequence; and (d) measuring the amount of said analyte bound to said solid support.

Also contemplates is a method of conducting a binding assay for a plurality of analytes comprising: (a) contacting a sample comprising a plurality of analytes with (i) a solid surface including one or more first binding reagents immobilized thereto, wherein said one or more first binding reagents each comprise a first binding region that binds to one or more of said analytes and each of said one or more first binding reagents are linked to one or more first linking agents each comprising a first oligonucleotide sequence; and (ii) one or more second binding reagents each comprising a second binding region that binds to one or more of said analytes and each of said one or more second binding reagents are linked to one or more second linking agents each comprising a second oligonucleotide sequence, wherein said second oligonucleotides sequence comprises a sequence complementary to at least a portion of said first oligonucleotides sequence; wherein said contacting step is conducted under conditions wherein said first and second binding regions that binds to said analytes and said first oligonucleotides sequence hybridizes to said second oligonucleotides sequence; and (c) measuring the amount of said analytes bound to said solid support.

The invention further provides a method of conducting a binding assay for a plurality of analytes comprising: (a) contacting a sample comprising a plurality of analytes with (i) a solid surface including one or more first binding reagents immobilized thereto, wherein said one or more first binding reagents each comprise a first binding region that binds to one or more of said analytes and each of said one or more first binding reagents are linked to one or more first linking agents each comprising a first oligonucleotide sequence; (b) contacting the mixture formed in step (a) with one or more second binding reagents each comprising a second binding region that binds to one or more of said analytes, wherein each of said one or more second binding reagents are linked to one or more a second linking agents each comprising a second oligonucleotide sequence, wherein said second oligonucleotide sequence comprises a sequence complementary to at least a portion of said first oligonucleotide sequence; wherein said contacting step (b) is conducted under conditions wherein said first and second binding regions bind to said analyte and said first oligonucleotide sequence hybridizes to said second oligonucleotide sequence; and (c) measuring the amount of said analyte bound to said solid support.

Alternatively, the methods of the invention include (a) contacting a sample comprising a plurality of analytes with (i) a solid surface including one or more first binding reagents immobilized thereto, wherein said one or more first binding reagents each comprise a first binding region that binds to said analytes and each of said one or more first binding reagents are linked to a first linking agent comprising a first oligonucleotide sequence; (ii) one or more second binding reagents each comprising a second binding region that binds to said analyte of interest, wherein said second binding reagent is linked to a second linking agent comprising a second oligonucleotide sequence, and (iii) one or more bridging oligonucleotide sequences each comprising a sequence complementary to at least a portion of said first oligonucleotide sequence and said second oligonucleotide sequence; wherein said contacting step is conducted under conditions wherein said first and second binding regions bind to said analytes and said bridging oligonucleotide sequences hybridizes to said first oligonucleotide sequence and said second oligonucleotide sequence; and (b) measuring the amount of said analytes bound to said solid support.

Also provided is a method of conducting a binding assay for a plurality of analytes comprising: (a) contacting a sample comprising a plurality of analytes with (i) a solid surface including one or more first binding reagents immobilized thereto, wherein said one or more first binding reagents each comprise a first binding region that binds to said analytes, wherein each of said first binding reagents are linked to a first linking agent comprising a first oligonucleotide sequence; and (ii) one or more second binding reagents each comprising a second binding region that binds to said analyte of interest, wherein said each of said one or more second binding reagents is linked to a second linking agent comprising a second oligonucleotide sequence, wherein said contacting step (a) is conducted under conditions wherein said first and second binding regions bind to said analytes; (b) contacting the mixture formed in step (b) with one or more bridging oligonucleotide sequences each comprising a sequence complementary to at least a portion of said first oligonucleotide sequence and said second oligonucleotide sequence; wherein said contacting step (c) is conducted under conditions wherein said bridging oligonucleotide sequences hybridize to said first oligonucleotide sequence and said second oligonucleotide sequence; and (c) measuring the amount of said analytes bound to said solid support.

Further included is a method of conducting a binding assay for a plurality of analytes comprising: (a) contacting a sample comprising a plurality of analytes with (i) a solid surface including one or more first binding reagents immobilized thereto, wherein said one or more first binding reagents each comprise a first binding region that binds to said analytes, wherein each of said first binding reagents is linked to a first linking agent comprising a first oligonucleotide sequence, wherein said contacting step (a) is conducted under conditions wherein said first binding region that binds to said analytes; (b) contacting the mixture formed in step (a) with one or more second binding reagents each comprising a second binding region that binds to said analytes, wherein said each of said one or more second binding reagents is linked to a second linking agent comprising a second oligonucleotide sequence, wherein said contacting step (b) is conducted under conditions wherein said second binding region binds to said analytes; (c) contacting the mixture formed in step (b) with one or more bridging oligonucleotide sequences comprising a sequence complementary to at least a portion of said first oligonucleotide sequence and said second oligonucleotide sequence; wherein said contacting step (c) is conducted under conditions wherein said one or more bridging oligonucleotide sequences hybridizes to said first oligonucleotide sequence and said second oligonucleotide sequence; and (d) measuring the amount of said analytes bound to said solid support.

The present invention also contemplates kits for the conduct of a binding assay comprising: (a) a solid surface including a first binding reagent immobilized thereto comprising a first binding region that binds to said analyte of interest, wherein said first binding reagent is linked to a first linking agent comprising a first oligonucleotide sequence; and (b) a second binding reagent comprising a second binding region that binds to said analyte of interest, wherein said second binding reagent is linked to a second linking agent comprising a second oligonucleotide sequence, wherein said second oligonucleotide sequence comprises a sequence complementary to at least a portion of said first oligonucleotide sequence.

Further, the kits of the invention may also comprise a solid surface including (i) a first binding reagent immobilized thereto comprising a first binding region that binds to said analyte of interest, wherein said first binding reagent is linked to a first linking agent comprising a first oligonucleotide sequence;

(ii) a second binding reagent comprising a second binding region that binds to said analyte of interest, wherein said second binding reagent is linked to a second linking agent comprising a second oligonucleotide sequence, and (iii) a bridging oligonucleotide sequence comprising a sequence complementary to at least a portion of said first oligonucleotide sequence and said second oligonucleotide sequence.

Moreover, the kits of the invention are configured to conduct a binding assay for a plurality of analytes and comprise (i) a solid surface including one or more first binding reagents immobilized thereto, wherein said one or more first binding reagents each comprise a first binding region that binds to one or more of said analytes and each of said one or more first binding reagents are linked to one or more first linking agents each comprising a first oligonucleotide sequence; and (ii) one or more second binding reagents each comprising a second binding region that binds to one or more of said analytes and each of said one or more second binding reagents are linked to one or more second linking agents each comprising a second oligonucleotide sequence, wherein said second oligonucleotides sequence comprises a sequence complementary to at least a portion of said first oligonucleotides sequence.

Another embodiment of a kit configured to conduct a binding assay for a plurality of analytes includes (i) a solid surface including one or more first binding reagents immobilized thereto, wherein said one or more first binding reagents each comprise a first binding region that binds to said analytes and each of said one or more first binding reagents are linked to a first linking agent comprising a first oligonucleotide sequence;

(ii) one or more second binding reagents each comprising a second binding region that binds to said analyte of interest, wherein said second binding reagent is linked to a second linking agent comprising a second oligonucleotide sequence, and (iii) one or more bridging oligonucleotide sequences each comprising a sequence complementary to at least a portion of said first oligonucleotide sequence and said second oligonucleotide sequence.

BRIEF DESCRIPTION OF DRAWINGS

FIGS. 1 (a)-(d) show various interactions between a capture antibody bound to a solid support and one or more species that may be present in a biological sample that may lead to undesired binding interactions and high background signals in an immunoassay. FIG. 1(a) shows a desired binding interaction between a capture antibody bound to a surface, bound to analyte A, which is bound to a labeled detection antibody. FIGS. 1(b)-(d) show undesired binding interactions. FIG. 1(b) shows a binding event between a capture antibody and a labeled detection antibody, FIG. 1(c) shows a binding event between a capture antibody and an extraneous analyte B, that may be present in a sample, and FIG. 1(d0 shows a binding event between a capture antibody and an additional antibody that may be present in the sample.

FIGS. 2(a)-(c) show the use of a bridging oligonucleotides sequence to facilitate a binding interaction in an immunoassay. FIG. 2(a) shows a bridge between a capture antibody, an analyte, A, and a detection antibody, wherein the bridging oligonucleotide includes a detectable label. FIG. 2(b) shows a bridge between a capture antibody, and an additional analyte in a sample, B, and FIG. 2(c) shows a binding interaction between a capture antibody, analyte B, and a detection antibody in the absence of a bridging oligonucleotide sequence.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The present invention improves the specificity of immunoassays by introducing a linking reagent that binds to a first binding reagent, e.g., a capture antibody, if the correct second binding reagent, e.g., a detection antibody, is present. Therefore, the invention provides a method of conducting a binding assay comprising contacting a sample including an analyte of interest with (i) a solid surface including a first binding reagent immobilized thereto comprising a first binding region that binds to the analyte of interest, wherein the first binding reagent is linked to a first linking agent comprising a first oligonucleotide sequence, and (ii) a second binding reagent comprising a second binding region that binds to the analyte of interest, wherein the second binding reagent is linked to a second linking agent comprising a second oligonucleotide sequence, wherein the second oligonucleotide sequence comprises a sequence complementary to at least a portion of the first oligonucleotide sequence. The contacting step is preferably conducted under conditions wherein the first and second binding regions bind to the analyte and the first oligonucleotide sequence hybridizes to the second oligonucleotide sequence. Therefore, in this embodiment, the first and second binding reagents are brought into proximity to one another via a first and second linking agent, respectively, bound to each of the binding reagents, wherein the linking agents include complementary oligonucleotides sequences.

In an alternative embodiment, the first and second binding reagents are brought into proximity via a bridging oligonucleotide sequence comprising a sequence complementary to at least a portion of the first linking agent and the second linking agent. Therefore, the invention provides a method of conducting a binding assay comprising (a) contacting a sample comprising an analyte of interest with (i) a solid surface including a first binding reagent immobilized thereto comprising a first binding region that binds to said analyte of interest, wherein said first binding reagent is linked to a first linking agent comprising a first oligonucleotide sequence;

(ii) a second binding reagent comprising a second binding region that binds to said analyte of interest, wherein said second binding reagent is linked to a second linking agent comprising a second oligonucleotide sequence, and (iii) a bridging oligonucleotide sequence comprising a sequence complementary to at least a portion of said first oligonucleotide sequence and said second oligonucleotide sequence; wherein said contacting step is conducted under conditions wherein said first and second binding regions bind to said analyte and said bridging oligonucleotide sequence hybridizes to said first oligonucleotide sequence and said second oligonucleotide sequence; and (b) measuring the amount of said analyte bound to said solid support.

In each embodiment, the linking and/or bridging oligonucleotide sequences are designed so that the binding interactions, i.e., between the first and second binding reagents and the linking or bridging sequence, are required for a stable attachment. Therefore, in the first embodiment of the invention in which the first and second binding reagents are held in proximity via an interaction between the first and second linking agents, a stable attachment forms when the first and second binding reagents bind to one another and the first linking agent binds to the complementary sequence of the second linking agent. If a bridging oligonucleotide sequence is employed, a stable attachment forms when the first and second binding reagents bind to one another and the bridging oligonucleotide sequence binds to its complement on the first and second linking agents.

In a preferred embodiment, the complementary sequence employed in the linking agent and/or bridging sequence is designed to have a relatively low binding energy such that a single interaction is insufficient to stably attach the linking agent to either of the binding reagents alone, but the combined avidity of simultaneous binding to the binding reagents is designed to be sufficient to stably bind the linking and/or bridging sequence. DNA oligonucleotides offer a conveniently adjustable and specific choice for the linking and/or bridging sequences. The binding energy can be adjusted by the length of the binding sequence, the temperature, and the salt concentration. Oligonucleotides also offer a convenient flexible tether between binding reagents and the length may be selected so that the linker or bridging sequence can bind the first and second binding reagents, e.g., capture and detection antibodies, as shown in FIG. 2.

The bridging/linking oligonucleotide sequence should be selected to be unique and as orthogonal as possible to other sequences in order to minimize unintended binding events. In one embodiment, the bridging/linking oligonucleotide sequence is about 5-20 bases in length, preferably 8-15 bases in length, more preferably about 8-12 bases in length and most preferably about 4-8 bases in length. The sequence and length will depend on the intended incubation temperature, salt concentration, and G/C content. In a preferred embodiment, the G/C content is between about 40-60%. The binding energy of individual pairings should be selected to be weak enough so that single oligonucleotides pairings is not stable on its own. Moreover, the linking/bridging sequence should be sufficiently long to allow for linkage/bridging between the first and second binding reagents. The oligonucleotide sequence may comprise a DNA sequence, e.g., poly-A or poly-T, or it could include additional moieties, e.g., polymer units such as ethylene glycol. In addition, the oligonucleotide sequences employed in the linking/bridging moieties need not be identical in length and in certain embodiments it may be beneficial to provide one oligonucleotide sequence that is longer than its binding partner, e.g., by up to 25 bases, or up to 15 bases, or up to 10 bases.

The methods of the present invention may involve one or more steps. For example, the binding assay may comprise:

(a) contacting a sample comprising an analyte of interest with (i) a solid surface including a first binding reagent immobilized thereto comprising a first binding region that binds to said analyte of interest, wherein said first binding reagent is linked to a first linking agent comprising a first oligonucleotide sequence and (ii) a second binding reagent comprising a second binding region that binds to said analyte of interest, wherein said second binding reagent is linked to a second linking agent comprising a second oligonucleotide sequence, wherein said second oligonucleotide sequence comprises a sequence complementary to at least a portion of said first oligonucleotide sequence; wherein said contacting step is conducted under conditions wherein said first and second binding regions bind to said analyte and said first oligonucleotide sequence hybridizes to said second oligonucleotide sequence; and (b) measuring the amount of said analyte bound to said solid support.

Alternatively, the method may involve a bridging oligonucleotide sequence, as follows:

(a) contacting a sample comprising an analyte of interest with (i) a solid surface including a first binding reagent immobilized thereto comprising a first binding region that binds to said analyte of interest, wherein said first binding reagent is linked to a first linking agent comprising a first oligonucleotide sequence; (ii) a second binding reagent comprising a second binding region that binds to said analyte of interest, wherein said second binding reagent is linked to a second linking agent comprising a second oligonucleotide sequence, and (iii) a bridging oligonucleotide sequence comprising a sequence complementary to at least a portion of said first oligonucleotide sequence and said second oligonucleotide sequence; wherein said contacting step is conducted under conditions wherein said first and second binding regions bind to said analyte and said bridging oligonucleotide sequence hybridizes to said first oligonucleotide sequence and said second oligonucleotide sequence; and (b) measuring the amount of said analyte bound to said solid support.

Still further, if a bridging oligonucleotides sequence is employed, the binding assay may involve a number of discrete steps, as follows:

(a) contacting a sample comprising an analyte of interest with (i) a solid surface including a first binding reagent immobilized thereto comprising a first binding region that binds to said analyte of interest, wherein said first binding reagent is linked to a first linking agent comprising a first oligonucleotide sequence, wherein said contacting step (a) is conducted under conditions wherein said first binding region binds to said analyte;

(b) contacting the mixture formed in step (a) with a second binding reagent comprising a second binding region that binds to said analyte of interest, wherein said second binding reagent is linked to a second linking agent comprising a second oligonucleotide sequence, wherein said contacting step (b) is conducted under conditions wherein said second binding region binds to said analyte;

(c) contacting the mixture formed in step (b) with a bridging oligonucleotide sequence comprising a sequence complementary to at least a portion of said first oligonucleotide sequence and said second oligonucleotide sequence; wherein said contacting step (c) is conducted under conditions wherein said bridging oligonucleotide sequence hybridizes to said first oligonucleotide sequence and said second oligonucleotide sequence; and (d) measuring the amount of said analyte bound to said solid support.

Still further, the method of the present invention may be applied to singleplex or multiplex formats where multiple assay measurements are performed on a single sample. Multiplex measurements may comprise the acts of contacting at least a portion of a sample with one or more binding surfaces comprising a plurality of binding domains, immobilizing one or more analytes on the domains and measuring the analytes immobilized on the domains. In certain embodiments, at least two of the binding domains differ in their specificity for analytes of interest. In one example of such an embodiment, the binding domains are prepared by immobilizing, on one or more surfaces, discrete domains of binding reagents that bind analytes of interest. Optionally, the sample is exposed to a binding surface that comprises an array of binding reagents. Optionally, the surface(s) may define, in part, one or more boundaries of a container (e.g., a flow cell, well, cuvette, etc.) which holds the sample or through which the sample is passed. The method may also comprise generating assay signals that are indicative of the amount of the analytes in the different binding domains, e.g., changes in optical absorbance, changes in fluorescence, the generation of chemiluminescence or electrochemiluminescence, changes in reflectivity, refractive index or light scattering, the accumulation or release of detectable labels from the domains, oxidation or reduction or redox species, electrical currents or potentials, changes in magnetic fields, etc.

In a preferred embodiment, a multiplexed assay method comprises:

(a) contacting a sample comprising a plurality of analytes with (i) a solid surface including one or more first binding reagents immobilized thereto, wherein said one or more first binding reagents each comprise a first binding region that binds to one or more of said analytes and each of said one or more first binding reagents are linked to one or more first linking agents each comprising a first oligonucleotide sequence; and (ii) one or more second binding reagents each comprising a second binding region that binds to one or more of said analytes and each of said one or more second binding reagents are linked to one or more second linking agents each comprising a second oligonucleotide sequence, wherein said second oligonucleotides sequence comprises a sequence complementary to at least a portion of said first oligonucleotides sequence; wherein said contacting step is conducted under conditions wherein said first and second binding regions bind to said analytes and said first oligonucleotides sequence hybridizes to said second oligonucleotides sequence; and (c) measuring the amount of said analytes bound to said solid support.

Alternatively, a multiplexed assay method may involve a bridging oligonucleotide sequence, as follows:

(a) contacting a sample comprising a plurality of analytes with (i) a solid surface including one or more first binding reagents immobilized thereto, wherein said one or more first binding reagents each comprise a first binding region that binds to said analytes and each of said one or more first binding reagents are linked to a first linking agent comprising a first oligonucleotide sequence; (ii) one or more second binding reagents each comprising a second binding region that binds to said analyte of interest, wherein said second binding reagent is linked to a second linking agent comprising a second oligonucleotide sequence, and (iii) one or more bridging oligonucleotide sequences each comprising a sequence complementary to at least a portion of said first oligonucleotide sequence and said second oligonucleotide sequence; wherein said contacting step is conducted under conditions wherein said first and second binding regions bind to said analytes and said bridging oligonucleotide sequences hybridizes to said first oligonucleotide sequence and said second oligonucleotide sequence; and (b) measuring the amount of said analytes bound to said solid support.

Moreover, the binding assay may include one or more washing steps. For example, once the sample and the first binding reagent are combined, the solid support may be washed prior to contacting the mixture with the second binding reagent and/or prior to introducing a bridging oligonucleotide.

The invention also contemplates a kit for the conduct of a binding assay comprising:

(a) a solid surface including a first binding reagent immobilized thereto comprising a first binding region that binds to said analyte of interest, wherein said first binding reagent is linked to a first linking agent comprising a first oligonucleotide sequence; and (ii) a second binding reagent comprising a second binding region that binds to said analyte of interest, wherein said second binding reagent is linked to a second linking agent comprising a second oligonucleotide sequence, wherein said second oligonucleotide sequence comprises a sequence complementary to at least a portion of said first oligonucleotide sequence.

Alternatively, the kit of the present invention may comprise a solid surface including (i) a first binding reagent immobilized thereto comprising a first binding region that binds to said analyte of interest, wherein said first binding reagent is linked to a first linking agent comprising a first oligonucleotide sequence;

(ii) a second binding reagent comprising a second binding region that binds to said analyte of interest, wherein said second binding reagent is linked to a second linking agent comprising a second oligonucleotide sequence, and (iii) a bridging oligonucleotide sequence comprising a sequence complementary to at least a portion of said first oligonucleotide sequence and said second oligonucleotide sequence.

Still further, the invention provides a kit for a multiplexed assay measurement for a plurality of analytes comprising (i) a solid surface including one or more first binding reagents immobilized thereto, wherein said one or more first binding reagents each comprise a first binding region that binds to one or more of said analytes and each of said one or more first binding reagents are linked to one or more first linking agents each comprising a first oligonucleotide sequence; and (ii) one or more second binding reagents each comprising a second binding region that binds to one or more of said analytes and each of said one or more second binding reagents are linked to one or more second linking agents each comprising a second oligonucleotide sequence, wherein said second oligonucleotides sequence comprises a sequence complementary to at least a portion of said first oligonucleotides sequence.

Alternatively, the kit may employ a bridging oligonucleotide to facilitate a multiplexed assay comprising:

(i) a solid surface including one or more first binding reagents immobilized thereto, wherein said one or more first binding reagents each comprise a first binding region that binds to said analytes and each of said one or more first binding reagents are linked to a first linking agent comprising a first oligonucleotide sequence;

(ii) one or more second binding reagents each comprising a second binding region that binds to said analyte of interest, wherein said second binding reagent is linked to a second linking agent comprising a second oligonucleotide sequence, and (iii) one or more bridging oligonucleotide sequences each comprising a sequence complementary to at least a portion of said first oligonucleotide sequence and said second oligonucleotide sequence.

Examples of samples that may be analyzed by the methods of the present invention include, but are not limited to food samples (including food extracts, food homogenates, beverages, etc.), environmental samples (e.g., soil samples, environmental sludges, collected environmental aerosols, environmental wipes, water filtrates, etc.), industrial samples (e.g., starting materials, products or intermediates from an industrial production process), human clinical samples, veterinary samples and other samples of biological origin. Biological samples that may be analyzed include, but are not limited to, feces, mucosal swabs, physiological fluids and/or samples containing suspensions of cells. Specific examples of biological samples include blood, serum, plasma, feces, mucosal swabs, tissue aspirates, tissue homogenates, cell cultures and cell culture supernatants (including cultures of eukaryotic and prokaryotic cells), urine, saliva, sputum, and cerebrospinal fluid.

Analytes that may be measured using the methods of the invention include, but are not limited to, proteins, toxins, nucleic acids, microorganisms, viruses, cells, fungi, spores, carbohydrates, lipids, glycoproteins, lipoproteins, polysaccharides, drugs, hormones, steroids, nutrients, metabolites and any modified derivative of the above molecules, or any complex comprising one or more of the above molecules or combinations thereof. The level of an analyte of interest in a sample may be indicative of a disease or disease condition or it may simply indicate whether the patient was exposed to that analyte.

The assays of the present invention may be used to determine the concentration of one or more, e.g., two or more analytes in a sample. Thus, two or more analytes may be measured in the same sample. Panels of analytes that can be measured in the same sample include, for example, panels of assays for analytes or activities associated with a disease state or physiological conditions. Certain such panels include panels of cytokines and/or their receptors (e.g., one or more of TNF-alpha, TNF-beta, IL1-alpha, IL1-beta, IL2, IL4, IL6, IL-10, IL-12, IFN-y, etc.), growth factors and/or their receptors (e.g., one or more of EGF, VGF, TGF, VEGF, etc.), drugs of abuse, therapeutic drugs, vitamins, pathogen specific antibodies, auto-antibodies (e.g., one or more antibodies directed against the Sm, RNP, SS-A, SS-alpha, J0-1, and Scl-70 antigens), allergen-specific antibodies, tumor markers (e.g., one or more of CEA, PSA, CA-125 II, CA 15-3, CA 19-9, CA 72-4, CYFRA 21-1, NSE, AFP, etc.), markers of cardiac disease including congestive heart disease and/or acute myocardial infarction (e.g., one or more of Troponin T, Troponin I, myoglobin, CKMB, myeloperoxidase, glutathione peroxidase, β-natriuretic protein (BNP), alpha-natriuretic protein (ANP), endothelin, aldosterone, C-reactive protein (CRP), etc.), markers associated with hemostasis (e.g., one or more of Fibrin monomer, D-dimer, thrombin-antithrombin complex, prothrombin fragments 1 & 2, anti-Factor Xa, etc.), markers of acute viral hepatitis infection (e.g., one or more of IgM antibody to hepatitis A virus, IgM antibody to hepatitis B core antigen, hepatitis B surface antigen, antibody to hepatitis C virus, etc.), markers of Alzheimers Disease (alpha-amyloid, beta-amyloid, Aβ 42, Aβ 40, Aβ 38, Aβ 39, Aβ 37, Aβ 34, tau-protein, etc.), markers of osteoporosis (e.g., one or more of cross-linked Nor C-telopeptides, total deoxypyridinoline, free deoxypyridinoline, osteocalcin, alkaline phosphatase, C-terminal propeptide of type I collagen, bone-specific alkaline phosphatase, etc.), markers of fertility state or fertility associated disorders (e.g., one or more of Estradiol, progesterone, follicle stimulating hormone (FSH), lutenizing hormone (LH), prolactin, hCG, testosterone, etc.), markers of thyroid disorders (e.g., one or more of thyroid stimulating hormone (TSH), Total T3, Free T3, Total T4, Free T4, and reverse T3), and markers of prostrate cancer (e.g., one or more of total PSA, free PSA, complexed PSA, prostatic acid phosphatase, creatine kinase, etc.). Certain embodiments of invention include measuring, e.g., one or more, two or more, four or more or 10 or more analytes associated with a specific disease state or physiological condition (e.g., analytes grouped together in a panel, such as those listed above; e.g., a panel useful for the diagnosis of thyroid disorders may include e.g., one or more of thyroid stimulating hormone (TSH), Total T3, Free T3, Total T4, Free T4, and reverse T3).

The methods of the present invention are designed to allow detection of a wide variety of biological and biochemical agents, as described above. In one embodiment, the methods may be used to detect pathogenic and/or potentially pathogenic virus, bacteria and toxins including biological warfare agents ("BWAs") in a variety of relevant clinical and environmental matrices, including and without limitation, blood, sputum, stool, filters, swabs, etc. A non-limiting list of pathogens and toxins that may be analyzed (alone or in combination) using the methods of the present invention is *Bacillus anthracis* (anthrax), *Yersinia pestis* (plague), *Vibrio cholerae* (cholera), *Francisella tularensis* (tularemia), *Brucella* spp. (Brucellosis), *Coxiella burnetii* (Q fever), orthopox viruses including variola virus (smallpox), viral encephalitis, Venezuelan equine encephalitis virus (VEE), western equine encephalitis virus (WEE), eastern equine encephalitis virus (EEE), Alphavirus, viral hemorrhagic fevers, Arenaviridae, Bunyaviridae, Filoviridae, Flaviviridae, Ebola virus, staphylococcal enterotoxins, ricin, botulinum toxins, *Clostridium botulinum*, mycotoxin, *Fusarium, Myrotecium, Cephalosporium, Trichoderma, Verticimonosporium, Stachybotrys*, glanders, wheat fungus, *Bacillus globigii, Serratia marcescens*, yellow rain, trichothecene mycotoxins, *Salmonella typhimurium*, aflatoxin, *Xenopsylla cheopis, Diamanus montanus*, alastrim, monkeypox, Arenavirus, Hantavirus, Lassa fever, Argentine hemorrhagic fevers, Bolivian hemorrhagic fevers, Rift Valley fever virus, Crimean-Congo virus, Hanta virus, Marburg hemorrhagic fevers, yellow fever virus, dengue fever viruses, influenza (including human and animal strains including H5N1 avian influenza), human immunodeficiency viruses I and II (HIV I and II), hepatitis A, hepatitis B, hepatitis C, hepatitis (non-A, B or C), Enterovirus, Epstein-Barr virus, Cytomegalovirus, herpes simplex viruses, *Chlamydia trachomatis, Neisseria gonorrheae, Trichomonas vaginalis*, human papilloma virus, *Treponema pallidum, Streptococcus pneumonia, Haemophilus influenzae, Mycoplasma pneumoniae, Chlamydophila pneumoniae, Legionella pneumophila, Staphylococcus aureus, Moraxella catarrhalis, Streptococcus pyogenes, Clostridium difficile, Neisseria meningitidis, Klebsiella pneumoniae, Mycobacterium tuberculosis*, coronavirus, Coxsackie A virus, rhinovirus, parainfluenza virus, respiratory syncytial virus (RSV), metapneumovirus, and adenovirus.

The skilled artisan in the field of binding assays will readily appreciate the scope of binding agents and companion binding partners that may be used in the present methods. A non-limiting list of such pairs include (in either order) receptor/ligand pairs, antibodies/antigens, natural or synthetic receptor/ligand pairs, amines and carbonyl compounds (i.e., binding through the formation of a Schiff's base), hapten/antibody pairs, antigen/antibody pairs, epitope/antibody pairs, mimitope/antibody pairs, aptamer/target molecule pairs, hybridization partners, and intercalater/target molecule pairs.

The binding assays of the methods of the present invention may employ antibodies or other receptor proteins as binding reagents. The term "antibody" includes intact antibody molecules (including hybrid antibodies assembled by in vitro re-association of antibody subunits), antibody fragments and recombinant protein constructs comprising an antigen binding domain of an antibody (as described, e.g., in Porter, R. R. and Weir, R. C. *J. Cell Physiol.*, 67 (Suppl): 51-64 (1966) and Hochman, 1. Inbar, D. and Givol, D. *Biochemistry* 12: 1130 (1973)), as well as antibody constructs that have been chemically modified, e.g., by the introduction of a detectable label.

The methods of the present invention may be used in a variety of assay devices and/or formats. The assay devices may include, e.g., assay modules, such as assay plates, cartridges, multi-well assay plates, reaction vessels, test tubes, cuvettes, flow cells, assay chips, lateral flow devices, etc., having assay reagents (which may include targeting agents or other binding reagents) added as the assay progresses or pre-loaded in the wells, chambers, or assay regions of the assay module. These devices may employ a variety of assay formats for specific binding assays, e.g., immunoassay or immunochromatographic assays. Illustrative assay devices and formats are described herein below. In certain embodiments, the methods of the present invention may employ assay reagents that are stored in a dry state and the assay devices/kits may further comprise or be supplied with desiccant materials for maintaining the assay reagents in a dry state. The assay devices preloaded with the assay reagents can greatly improve the speed and reduce the complexity of assay measurements while maintaining excellent stability during storage. The dried assay reagents may be any assay reagent that can be dried and then reconstituted prior to use in an assay. These include, but are not limited to, binding reagents useful in binding assays, enzymes, enzyme substrates, indicator dyes and other reactive compounds that may be used to detect an analyte of interest. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of compartments (e.g., chambers, channels, flow cells, wells, etc.) in the assay modules or the surfaces of colloids, beads, or other particulate supports.

A wide variety of solid phases are suitable for use in the methods of the present invention including conventional solid phases from the art of binding assays. Solid phases may be made from a variety of different materials including polymers (e.g., polystyrene and polypropylene), ceramics, glass, composite materials (e.g., carbon-polymer composites such as carbon-based inks). Suitable solid phases include the surfaces of macroscopic objects such as an interior surface of an assay container (e.g., test tubes, cuvettes, flow cells, cartridges, wells in a multi-well plate, etc.), slides, assay chips (such as those used in gene or protein chip measurements), pins or probes, beads, filtration media, lateral flow media (for example, filtration membranes used in lateral flow test strips), etc.

Suitable solid phases also include particles (including but not limited to colloids or beads) commonly used in other types of particle-based assays e.g., magnetic, polypropylene, and latex particles, materials typically used in solid-phase synthesis e.g., polystyrene and polyacrylamide particles, and materials typically used in chromatographic applications e.g., silica, alumina, polyacrylamide, polystyrene. The materials may also be a fiber such as a carbon fibril. Microparticles may be inanimate or alternatively, may include animate biological entities such as cells, viruses, bacterium and the like.

The particles used in the present method may be comprised of any material suitable for attachment to one or more binding partners and/or labels, and that may be collected via, e.g., centrifugation, gravity, filtration or magnetic collection.

A wide variety of different types of particles that may be attached to binding reagents are sold commercially for use in binding assays. These include non-magnetic particles as well as particles comprising magnetizable materials which allow the particles to be collected with a magnetic field. In one embodiment, the particles are comprised of a conductive and/or semiconductive material, e.g., colloidal gold particles.

The microparticles may have a wide variety of sizes and shapes. By way of example and not limitation, microparticles may be between 5 nanometers and 100 micrometers. Preferably microparticles have sizes between 20 nm and 10 micrometers. The particles may be spherical, oblong, rod-like, etc., or they may be irregular in shape.

The particles used in the present method may be coded to allow for the identification of specific particles or subpopulations of particles in a mixture of particles. The use of such coded particles has been used to enable multiplexing of assays employing particles as solid phase supports for binding assays. In one approach, particles are manufactured to include one or more fluorescent dyes and specific populations of particles are identified based on the intensity and/or relative intensity of fluorescence emissions at one or more wave lengths. This approach has been used in the Luminex xMAP systems (see, e.g., U.S. Pat. No. 6,939,720) and the Becton Dickinson Cytometric Bead Array systems. Alternatively, particles may be coded through differences in other physical properties such as size, shape, imbedded optical patterns and the like.

The methods of the invention can be used with a variety of methods for measuring the amount of an analyte and, in particular, measuring the amount of an analyte bound to a solid phase. Techniques that may be used include, but are not limited to, techniques known in the art such as cell culture-based assays, binding assays (including agglutination tests, immunoassays, nucleic acid hybridization assays, etc.), enzymatic assays, colorometric assays, etc. Other suitable techniques will be readily apparent to one of average skill in the art. Some measurement techniques allow for measurements to be made by visual inspection, others may require or benefit from the use of an instrument to conduct the measurement.

Methods for measuring the amount of an analyte include label free techniques, which include but are not limited to i) techniques that measure changes in mass or refractive index at a surface after binding of an analyte to a surface (e.g., surface acoustic wave techniques, surface plasmon resonance sensors, ellipsometric techniques, etc.), ii) mass spectrometric techniques (including techniques like MALDI, SELDI, etc. that can measure analytes on a surface), iii) chromatographic or electrophoretic techniques, iv) fluorescence techniques (which may be based on the inherent fluorescence of an analyte), etc.

Methods for measuring the amount of an analyte also include techniques that measure analytes through the detection of labels which may be attached directly or indirectly (e.g., through the use of labeled binding partners of an analyte) to an analyte. Suitable labels include labels that can be directly visualized (e.g., particles that may be seen visually and labels that generate an measurable signal such as light scattering, optical absorbance, fluorescence, chemiluminescence, electrochemiluminescence, radioactivity, magnetic fields, etc). Labels that may be used also include enzymes or other chemically reactive species that have a chemical activity that leads to a measurable signal such as light scattering, absorbance, fluorescence, etc. The use of enzymes as labels has been well established in in Enzyme-Linked ImmunoSorbent Assays, also called ELISAs, Enzyme ImmunoAssays or EIAs. In the ELISA format, an unknown amount of antigen is affixed to a surface and then a specific antibody is washed over the surface so that it can bind to the antigen. This antibody is linked to an enzyme, and in the final step a substance is added that the enzyme converts to a product that provides a change in a detectable signal. The formation of product may be detectable, e.g., due a difference, relative to the substrate, in a measurable property such as absorbance, fluorescence, chemiluminescence, light scattering, etc. Certain (but not all) measurement methods that may be used with solid phase binding methods according to the invention may benefit from or require a wash step to remove unbound components (e.g., labels) from the solid phase Accordingly, the methods of the invention may comprise such a wash step.

In one embodiment, the detection antibody includes a detectable label attached thereto. Alternatively, a bridging oligonucleotide is employed and the bridging oligonucleotide includes a detectable label. As shown in FIGS. 2(a)-(c), the desired binding interaction is detected if the bridging oligonucleotide is in position between the first and second linking agents and the bridging sequence also bears the detectable label.

In one embodiment, an analyte(s) of interest in the sample may be measured using electrochemiluminescence-based assay formats, e.g. electrochemiluminescence (ECL) based immunoassays. The high sensitivity, broad dynamic range and selectivity of ECL are important factors for medical diagnostics. Commercially available ECL instruments have demonstrated exceptional performance and they have become widely used for reasons including their excellent sensitivity, dynamic range, precision, and tolerance of complex sample matrices. Species that can be induced to emit ECL (ECL-active species) have been used as ECL labels, e.g., i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485), oxalate, and persulfate for ECL from RuBpy and hydrogen peroxide for ECL from luminol (see, e.g., U.S. Pat. No. 5,240,863). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093,268; 5,147, 806; 5,324,457; 5,591,581; 5,597,910; 5,641,623; 5,643, 713; 5,679,519; 5,705,402; 5,846,485; 5,866,434; 5,786, 141; 5,731,147; 6,066,448; 6,136,268; 5,776,672; 5,308, 754; 5,240,863; 6,207,369; 6,214,552 and 5,589,136 and Published PCT Nos. WO99/63347; WOOO/03233; WO99/ 58962; WO99/32662; WO99/14599; WO98/12539; WO97/ 36931 and WO98/57154, all of which are incorporated herein by reference.

The methods of the invention may be applied to single-plex or multiplex formats where multiple assay measurements are performed on a single sample. Multiplex measurements that can be used with the invention include, but are not limited to, multiplex measurements i) that involve the use of multiple sensors; ii) that use discrete assay domains on a surface (e.g., an array) that are distinguishable based on location on the surface; iii) that involve the use of reagents coated on particles that are distinguishable based on a particle property such as size, shape, color, etc.; iv) that produce assay signals that are distinguishable based on optical properties (e.g., absorbance or emission spectrum) or v) that are based on temporal properties of assay signal (e.g., time, frequency or phase of a signal).

One embodiment of the present invention employs a specific binding assay, e.g., an immunoassay, immunochromatographic assay or other assay that uses a binding reagent. The immunoassay or specific binding assay according to one embodiment of the invention can involve a number of formats available in the art. The binding reagents can be labeled with a label or immobilized on a surface. Thus, in one embodiment, the detection method is a binding assay, e.g., an immunoassay, receptor-ligand binding assay or hybridization assay, and the detection is performed by contacting an assay composition with one or more detection molecules capable of specifically binding with an analyte(s) of interest in the sample.

In one embodiment, the assay uses a direct binding assay format. An analyte is bound to a binding partner of the analyte, which may be immobilized on a solid phase. The bound analyte is measured by direct detection of the analyte or through a label attached to the analyte (e.g., by the measurements described above).

The present invention is not to be limited in scope by the specific embodiments described herein. Indeed, various modifications of the method in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A method of conducting a binding assay comprising:
   (a) contacting a sample comprising an analyte of interest with (i) a solid surface including a first binding reagent immobilized thereto comprising a first binding region that binds to said analyte of interest, wherein said first binding reagent is linked to a first linking agent comprising a first oligonucleotide sequence and (ii) a second binding reagent comprising a second binding region that binds to said analyte of interest, wherein said second binding reagent is linked to a second linking agent comprising a second oligonucleotide sequence, wherein said second oligonucleotide sequence comprises a sequence complementary to at least a portion of said first oligonucleotide sequence, wherein said second binding reagent is not immobilized to said solid surface; wherein said contacting step is conducted under conditions wherein said first and second binding regions bind to said analyte and said first oligonucleotide sequence hybridizes to said second oligonucleotide sequence, wherein said first and second linking agents are configured such that under said conditions, a binding energy between the first oligonucleotide sequence and the second oligonucleotide sequence is below a level to stably attach the first oligonucleotide sequence and the second oligonucleotide sequence to each other in the absence of simultaneous binding of the first and second binding regions to the analyte; and
   (b) measuring the amount of said analyte bound to said solid support.

2. A method of conducting a binding assay comprising:
   (a) contacting a sample comprising an analyte of interest with a solid surface including a first binding reagent immobilized thereto comprising a first binding region that binds to said analyte of interest, wherein said first binding reagent is linked to a first linking agent comprising a first oligonucleotide sequence;
   (b) contacting the mixture formed in step (a) with a second binding reagent comprising a second binding region that binds to said analyte of interest, wherein said second binding reagent is linked to a second linking agent comprising a second oligonucleotide sequence, wherein said second oligonucleotide sequence comprises a sequence complementary to at least a portion of said first oligonucleotide sequence, wherein said second binding reagent is not immobilized to said solid surface; wherein said contacting step (b) is conducted under conditions wherein said first and second binding regions bind to said analyte and said first oligonucleotide sequence hybridizes to said second oligonucleotide sequence, wherein said first and second linking agents are configured such that under said conditions, a binding energy between the first oligonucleotide sequence and the second oligonucleotide sequence is below a level to stably attach the first oligonucleotide sequence and the second oligonucleotide sequence to each other in the absence of simultaneous binding of the first and second binding regions to the analyte; and
   (b) measuring the amount of said analyte bound to said solid support.

3. A method of conducting a binding assay for a plurality of analytes comprising:
   (a) contacting a sample comprising a plurality of analytes with (i) a solid surface including one or more first binding reagents immobilized thereto, wherein said one or more first binding reagents each comprise a first binding region that binds to one or more of said analytes and each of said one or more first binding reagents are linked to one or more first linking agents each comprising a first oligonucleotide sequence; and (ii) one or more second binding reagents each comprising a second binding region that binds to one or more of said analytes and each of said one or more second binding reagents are linked to one or more second linking agents each comprising a second oligonucleotide sequence, wherein said second oligonucleotides sequence comprises a sequence complementary to at least a portion of said first oligonucleotides sequence, wherein said second binding reagent is not immobilized to said solid surface; wherein said contacting step is conducted under conditions wherein said first and second binding regions bind to said analytes and said first oligonucleotides sequence hybridizes to said second oligonucleotides sequence, wherein said first and second linking agents are configured such that under said conditions, a binding energy between the first oligonucleotide sequence and the second oligonucleotide sequence is below a level to stably attach the first oligonucleotide sequence and the second oligonucleotide sequence to each other in the absence of simultaneous binding of the first and second binding regions to the analyte; and (c) measuring the amount of said analytes bound to said solid support.

4. A method of conducting a binding assay for a plurality of analytes comprising:

(a) contacting a sample comprising a plurality of analytes with (i) a solid surface including one or more first binding reagents immobilized thereto, wherein said one or more first binding reagents each comprise a first binding region that binds to one or more of said analytes and each of said one or more first binding reagents are linked to one or more first linking agents each comprising a first oligonucleotide sequence;

(b) contacting the mixture formed in step (a) with one or more second binding reagents each comprising a second binding region that binds to one or more of said analytes, wherein each of said one or more second binding reagents are linked to one or more second linking agents each comprising a second oligonucleotide sequence, wherein said second oligonucleotide sequence comprises a sequence complementary to at least a portion of said first oligonucleotide sequence, wherein said second binding reagent is not immobilized to said solid surface; wherein said contacting step (b) is conducted under conditions wherein said first and second binding regions bind to said analyte and said first oligonucleotide sequence hybridizes to said second oligonucleotide sequence, wherein said first and second linking agents are configured such that under said conditions, a binding energy between the first oligonucleotide sequence and the second oligonucleotide sequence is below a level to stably attach the first oligonucleotide sequence and the second oligonucleotide sequence to each other in the absence of simultaneous binding of the first and second binding regions to the analyte; and (c) measuring the amount of said analyte bound to said solid support.

5. The method of claim 1 wherein said first binding region is specific for said analyte of interest.

6. The method of claim 1 wherein said second binding region is specific for said analyte of interest.

7. The method claim 1 wherein said first binding reagent is an antibody.

8. The method of claim 1 wherein said second binding reagent is an antibody.

9. The method of claim 1 wherein said measuring step comprises measuring optical absorbance, fluorescence, phosphorescence, chemiluminescence, light scattering or magnetism.

10. The method of claim 1 wherein said second binding reagent comprises a detectable label.

11. The method of claim 1 wherein said solid support is an electrode and said measuring step further comprises applying a voltage waveform to said electrode to generate electrochemiluminescense (ECL).

12. The method of claim 1 wherein said first oligonucleotide sequence comprises about 5-15 bases.

13. The method of claim 1 wherein said second oligonucleotide sequence comprises about 5-15 bases.

14. The method of claim 1 wherein said first oligonucleotide sequence and said second oligonucleotide sequence each comprise a complementary binding sequence of about 4-8 bases in length.

15. The method of claim 1, wherein said solid surface is selected from the group consisting of a surface of a flow cell, a surface of a particle, a surface of a cartridge, and a well of a multiwell plate.

16. The method of claim 2, wherein said solid surface is selected from the group consisting of a surface of a flow cell, a surface of a particle, a surface of a cartridge, and a well of a multiwell plate.

17. The method of claim 3, wherein said solid surface is selected from the group consisting of a surface of a flow cell, a surface of a particle, a surface of a cartridge, and a well of a multiwell plate.

18. The method of claim 4, wherein said solid surface is selected from the group consisting of a surface of a flow cell, a surface of a particle, a surface of a cartridge, and a well of a multiwell plate.

19. The method of claim 1, wherein said second linking agent further comprises a polymer unit.

20. The method of claim 2, wherein said second linking agent further comprises a polymer unit.

21. The method of claim 3, wherein said second linking agent further comprises a polymer unit.

22. The method of claim 4, wherein said second linking agent further comprises a polymer unit.

23. The method of claim 2, wherein said measuring step comprises measuring optical absorbance, fluorescence, phosphorescence, chemiluminescence, light scattering or magnetism.

24. The method of claim 2, wherein said second binding reagent comprises a detectable label.

25. The method of claim 2, wherein said first linking agent further comprises a polymer unit.

26. The method of claim 2, wherein a length of both the first oligonucleotide sequence and the second oligonucleotide sequence is 4-8 bases in length.

27. The method of claim 3, wherein said measuring step comprises measuring optical absorbance, fluorescence, phosphorescence, chemiluminescence, light scattering or magnetism.

28. The method of claim 3, wherein said second binding reagent comprises a detectable label.

29. The method of claim 3, wherein said first linking agent further comprises a polymer unit.

30. The method of claim 3, wherein a length of both the first oligonucleotide sequence and the second oligonucleotide sequence is 4-8 bases in length.

31. The method of claim 4, wherein said measuring step comprises measuring optical absorbance, fluorescence, phosphorescence, chemiluminescence, light scattering or magnetism.

32. The method of claim 4, wherein said second binding reagent comprises a detectable label.

33. The method of claim 4, wherein said first linking agent further comprises a polymer unit.

34. The method of claim 4, wherein a length of both the first oligonucleotide sequence and the second oligonucleotide sequence is 4-8 bases in length.

* * * * *